(12) United States Patent
Benner et al.

(10) Patent No.: US 10,654,841 B1
(45) Date of Patent: May 19, 2020

(54) PROCESSES WITH TERMINAL TRANSFERASE, AMINOXY NUCLEOSIDE TRIPHOSPHATES, AND NUCLEOBASE ANALOGS (71) Applicants: Steven A Benner, Gainesville, FL (US); Nicole A Leal, Gainesville, FL (US)

(72) Inventors: Steven A Benner, Gainesville, FL (US); Nicole A Leal, Gainesville, FL (US)

( * ) Notice: Subject to any disclaimer, the term of this patent is extended or adjusted under 35 U.S.C. 154(b) by 0 days.

(21) Appl. No.: 15/786,086

(22) Filed: Oct. 17, 2017

Related U.S. Application Data (63) Continuation-in-part of application No. 15/745,694, filed on Mar. 31, 2017, now abandoned.

(51) Int. Cl.
*C07D 413/14* (2006.01)
*C12P 19/34* (2006.01)
*C07H 21/04* (2006.01)

(52) U.S. Cl.
CPC ........... *C07D 413/14* (2013.01); *C07H 21/04* (2013.01); *C12P 19/34* (2013.01); *C12N 2310/33* (2013.01)

(58) Field of Classification Search
CPC .............. C12Q 2525/313; A61K 38/00; C12N 15/113; C12N 15/102; C12P 9/34
USPC ................................. 435/6.1, 6.11; 536/23.2
See application file for complete search history.

(56) References Cited

PUBLICATIONS

Sismour et al. Nucl. Acids Res. 2004, V 32, pp. 728-735.*

* cited by examiner

*Primary Examiner* — Robert B Mondesi
*Assistant Examiner* — Mohammad Y Meah (57) ABSTRACT This invention claims processes that comprise the appending of nucleotides having a 3'-$ONH_2$ moiety to the 3'-ends of oligonucleotide primers using 3'-deoxynucleoside triphosphates of 2'-deoxynucleoside derivatives that have, instead of a 3'-OH moiety, a 3'-$ONH_2$ moiety, where the nucleotides contain non-standard nucleobases.

6 Claims, 9 Drawing Sheets

Specification includes a Sequence Listing.

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gcgtaatacg actcactatg gacg    24

PROCESSES WITH TERMINAL TRANSFERASE, AMINOXY NUCLEOSIDE TRIPHOSPHATES, AND NUCLEOBASE ANALOGS

CROSS REFERENCE TO RELATED APPLICATIONS

This is a continuation in part of U.S. patent application Ser. No. 15/475,694, filed 31 Mar. 2017.

STATEMENT OF RIGHTS TO INVENTIONS MADE UNDER FEDERALLY-SPONSORED RESEARCH

This invention was made with government support under R41GM119494 awarded by the National Institutes of General Medical Sciences. The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

This invention relates to the field of nucleic acid chemistry, more specifically to analogs of nucleoside triphosphates whose 3'-oxygen atoms are covalently bonded to a moiety that does not allow an oligonucleotide having that nucleotide at its 3'-end to be extended unless that moiety is removed. This moiety is called a "reversible terminator", a phrase also used in the art to refer to the triphosphate and the nucleotide derived from the triphosphate once incorporated at the 3'-end of an oligonucleotide chain. Still more specifically, this invention relates to processes where the moiety attached to the 3'-triphosphate oxygen is an amino group; in this case, the triphosphate analog is said to be an "aminoxy" triphosphate. Still more specifically this invention relates to processes where terminal deoxynucleotide transferase uses the reversibly terminating nucleoside triphosphate to add a 3'-aminoxy-2',3'-dideoxynucleotide to the 3'-end of a DNA molecule.

(2) Description of Related Art

Well-known in the art are useful processes that require that the enzymatic extension of a DNA or RNA oligonucleotide be terminated after introduction of a single nucleotide at the 3'-end.

This extension may be templated, as in the primer-extension processes that are catalyzed by DNA polymerases, RNA polymerases, or reverse transcriptases. Here, termination is the process underlying many DNA sequencing architectures. Termination of template-guided extension after the addition of a single nucleotide is frequently achieved by contacting the enzyme to analog of a nucleoside triphosphate where the nucleoside has been altered so as to no longer have a free 3'-hydroxyl group.

Well known among these analogs are triphosphates where the 3'-hydroxyl group is replaced by a hydrogen atom to generate 2',3'-dideoxynucleoside triphosphates. These are substrates for many polymerases, including many modified polymerases. In forms that carry side chains carrying reporter groups, these have long been used in DNA sequencing processes. Since no convenient method is available to replace the 3'-H by a 3'-OH group on an oligonucleotide, the termination of the oligonucleotide extension process in the presence of a 2',3'-dideoxynucleoside triphosphate analog is said to be irreversible.

Other nucleoside and oligonucleotide derivatives lacking the standard 3'-OH have functionality that can later be converted to a 3'-OH group under conditions that do not damage oligonucleotides. This allows template-directed primer extension to be terminated "reversibly".

For example, various patents, including U.S. Pat. Nos. 7,544,794, 8,034,923, and 8,212,020, disclosed that a 3'-O—$NH_2$ group may be used a reversibly terminating moiety. These are referred to as 3'-aminoxy-2',3'-dideoxynucleosides, -tides, and triphosphates. After a nucleotide having a 3'-O—$NH_2$ group is added to the 3'-end of an oligonucleotide primer, further polymerase-catalyzed extension cannot occur.

This terminating 3'-O—$NH_2$ group may not be removed, allowing its reactivity to be used for a variety of purposes. For example, the 3'-O—$NH_2$ group can react with another molecule that carries an aldehyde or ketone moiety to form useful oximes.

However, if the appropriate reagents are added, the nitrogen-oxygen bond of the 3'-O—$NH_2$ group can be cleaved, thereby converting the 3'-O$NH_2$ group to a 3'-OH group. Once converted, enzymatic extension can proceed. U.S. Pat. Nos. 7,544,792 and 8,212,020 did not provide a practical reagent for cleaving the nitrogen-oxygen bond in the 3'-O—$NH_2$ unit in an oligonucleotide to generate an extendable 3'-OH group, U.S. Pat. No. 8,034,923 did. U.S. Pat. No. 8,034,923 taught that the nitrogen-oxygen bond in the 3'-O—$NH_2$ unit could be cleaved by an aqueous solution of sodium nitrite buffered to a pH of near six. The product of that cleavage reaction is a 3'-OH group.

Unfortunately, as taught in U.S. patent application Ser. No. 15/460,475 (Benner, S. A. (2017) Nucleoside Triphosphates with Stable Aminoxy Groups. Filed 16 Mar. 2017), whose disclosure is reported in its entirety herein by reference, these earlier disclosures did not provide sufficiently pure 3'-$ONH_2$ terminated triphosphates for these species to have the maximum utility. Specifically, all the preparations disclosed, intrinsically based on the method of their preparation, contained small but substantial amounts of 3'-nucleoside triphosphates having unblocked 3'-OH groups, here defined as 0.5% or greater. Thus, use of these in template reactions frequently did not lead to termination of all oligonucleotide chains.

The same is the case with untemplated oligonucleotide elongation. This is catalyzed by the enzyme known as terminal deoxynucleotide transferase (TdT, or, often terminal transferase).

Again, the contaminating 3'-nucleoside triphosphates having free 3'-OH groups would lead to products with two or more nucleotides added to the 3'-end of the extending oligonucleotide. This led to mixtures of products, especially because many natural terminal transferases prefer natural unblocked 3'-OH nucleoside triphosphates over those carrying a 3'-$ONH_2$ terminating group.

BRIEF SUMMARY OF THE INVENTION

This invention is based on the discovery that a 3'-aminoxy-2',3'-dideoxynucleotide (hereinafter, aminoxy nucleotide) can be added to the 3'-end of an oligonucleotide in an untemplated process. This invention is rendered useful by the availability of 3'-aminoxy nucleoside triphosphates substantially free of 3'-nucleoside triphosphates having unblocked 3'-OH groups. These are made available for the first time by the processes disclosed in U.S. patent application Ser. No. 15/460,475 (for Nucleoside Triphosphates with Stable Aminoxy Groups, filed 16 Mar. 2017), whose disclosure is incorporated herein in its entirety by reference.

DETAILED DESCRIPTION OF THE INVENTION

The invention disclosed here involves contacting an oligonucleotide in an appropriate buffer with an enzyme known as terminal deoxynucleotide transferase (TdT, or simply terminal transferase). Terminal transferase was discovered many years ago in calf thymus as an enzyme that adds nucleoside triphosphates to the 3'-end of an oligonucleotide in an untemplated fashion.

Some key references, which are incorporated herein by citation, are:
Roychoudhury, R., Jay, E., Wu, R. (1976) *Nucl. Acids Res.* 3, 101-116.
Tu, C. P., Cohen, S. N. (1980) *Gene.* 10, 177-183.
Boule, J. B., Rougeon, F., Papanicolaou, C. (2001) *J. Biol. Chem.* 276, 31388-31393.

The presently preferred terminal deoxynucleotidyl transferase (TdT) prefers DNA as an oligonucleotide substrate. Single ribonucleotide addition is seen with the native enzyme a slower rate. The presently preferred TdT is the enzyme that is commercially available, recently sold by New England Biolabs or Promega, or the analogous enzyme obtained from other mammalian thymus glands. Most preferred is a TdT or one of its variants containing 1-3 amino acid replacements obtained via recombinant DNA technology that is expressed in a host cell.

The invention here comprises contacting of an oligonucleotide, preferably a 3'-oligodeoxyribonucleotide, with a triphosphate, as disclosed in U.S. Pat. No. 8,034,923, carrying the 3'-$ONH_2$ moiety, in aqueous buffers where TdT operates. These buffers are well known in the art, and are provided in the examples below. The buffer may optionally contain divalent cobalt cation ($Co^{++}$), which is known to improve the ability of the terminal transferase to accept standard pyrimidine nucleoside triphosphates. However, with the aminoxy analogs, we have discovered that $Co^{++}$ does not improve the performance of TdT, at least in the buffers examined. Those buffers have preferable pH ranges from 7 to 8, but not outside pH 6 to 9. The preferable contact temperature is preferably between 25° C. and 40° C.

The utility of the instant invention arises from its ability to at a single nucleotide at a time. This can be, for example, envisioned as a synthesis procedure, where an oligonucleotide having a defined, preselected, sequence is synthesized by contacting an immobilized primer with:

(a) a nucleoside triphosphate having a 3'-$ONH_2$ moiety and carrying the nucleobase of the desired first nucleotide in the preselected sequence, (b) incubating for a period of time to allow the single nucleotide addition to go substantially to completion, (c) washing the incubation mixture from the immobilized primer which now has additional nucleotide and a blocked 3'-end, (d) removing the 3'-aminoxy block, for example, by treating with buffered sodium nitrite following the procedure described in U.S. Pat. No. 8,034,923 (Benner, S. A., Hutter, D., Leal, N. A., Chen, F. *Reagents for Reversibly Terminating Primer extension.* U.S. Pat. No. 8,034,923), which is incorporated in its entirety by reference, and (e) repeating the cycle for each additional desired nucleotide in the preselected sequence.

For this and other applications where addition of precisely one nucleotide is desired, is preferred that the triphosphate having a 3'-$ONH_2$ moiety not be contaminated with triphosphates that have a standard, and extendable, 3'-OH group. As shown in the examples, TdT has a preference for the natural triphosphate having an extendable 3'-OH group. Indeed, TdT can be used to clean up preparations of triphosphates having a 3'-ONH$_2$ moiety by removing natural triphosphates having an extendable 3'-OH group. For other applications, this contamination is tolerable.

Figure 5:
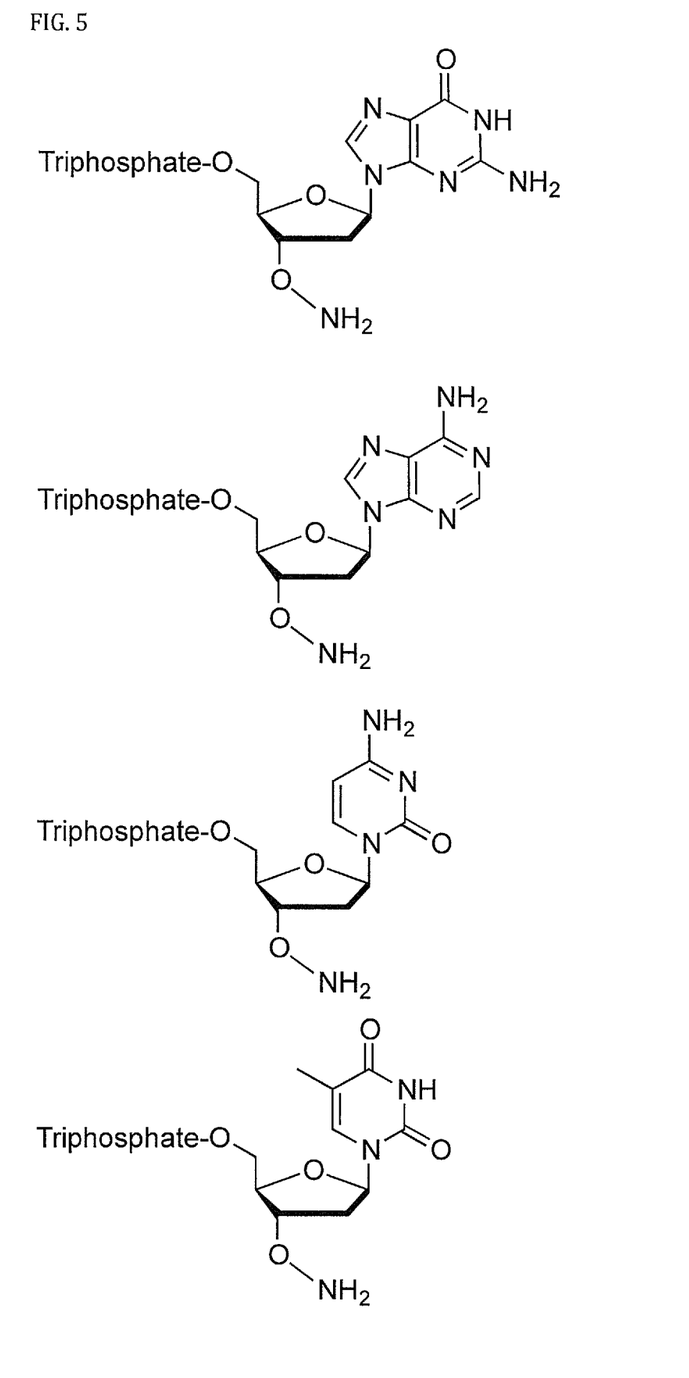
FIG. 5. Structures of the standard 3'-aminoxytriphosphates of the instant invention.
Figure 6:
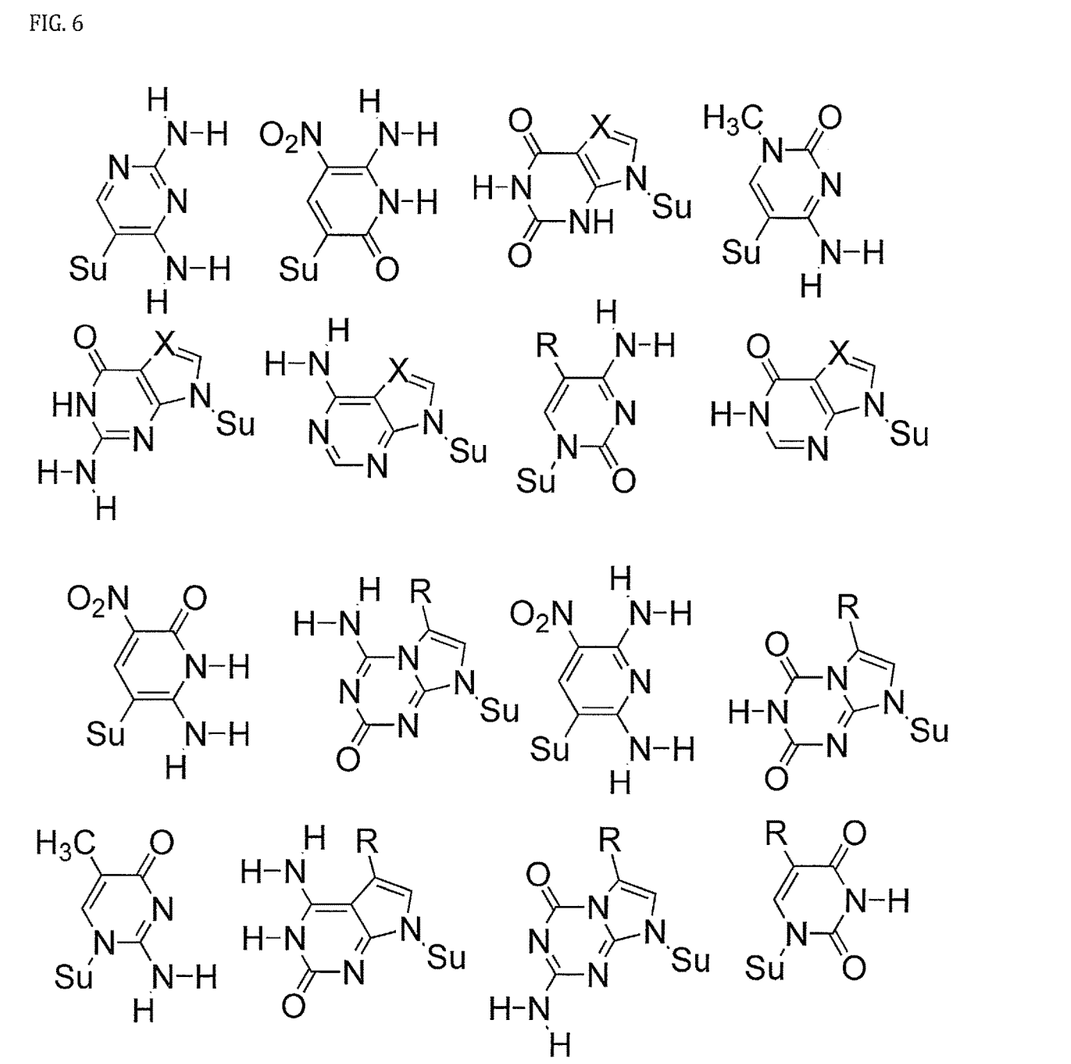
FIG. 6. Structures of the standard and non-standard 3'-aminoxytriphosphates of the instant invention, where Su indicates the point of attachment of the heterocycle to the sugar, R is either H, $CH_3$, or a functionalized side chain, and X is either N or C—R.

The most presently preferred triphosphates having a 3'-ONH$_2$ moiety are those prepared by the procedure disclosed in U.S. patent application Ser. No. 15/460,475, which is incorporated herein in its entirety by reference. These nucleoside triphosphates are substantially free of contaminating standard triphosphate, where "substantially" means that the preparation triphosphate carrying a 3'-O—NH$_2$ moiety contains less than 0.5 mole percent of the analogous triphosphate with a free 3'-OH group, more preferably less than 0.05 mole percent, and most preferably less than 0.005 mole percent, calculated relative to the triphosphate carrying a 3'-O—NH$_2$ moiety. Further, as taught in U.S. patent application Ser. No. 15/460,475, in addition to the standard nucleoside triphosphates shown in FIG. 5, the nucleoside might carry an unnatural nucleobase, selected from the structures shown in FIG. 6.

EXAMPLES

Example 1

The ability of terminal transferase to add a 3'-aminoxy terminating triphosphate to oligonucleotides was discovered by a series of experiments. In these experiments, this oligonucleotide substrate was used:

```
dhSSP1:
                                          SEQ ID NO 1
5'-GCG TAA TAC GAC TCA CTA TGG ACG-3'
```

This oligonucleotide was 5'-labeled to give

```
5'-$^{32}$P-GCG TAA TAC GAC TCA CTA TGG ACG-3',
``` which is SEQ ID NO 1) using OptiKinase and gamma-labeled radioactive ATP.

Two different buffers were used for the experiments that discovered the ability of terminal transferase to add a 3'-aminoxy terminating triphosphate to oligonucleotides. The "purine tailing buffer" contained 100 mM cacodylate buffer (pH 7.1), 2 mM MnCl$_2$, 0.1 mM DTT, 10 pmol of radiolabeled template (0.5 µM), 10 units of Terminal Transferase, and varying amounts of reversible terminating triphosphates ranging from 5 µM to 250 µM (as indicated on gel). The total volume was 20 µL.

The "pyrimidine tailing buffer" contained 100 mM cacodylate buffer (pH 7.1), 2 mM CoCl$_2$, 0.1 mM DTT, 10 pmol of radiolabeled template (0.5 µM), 10 units of Terminal Transferase, and varying amounts of reversible terminator triphosphates from 5 µM to 250 µM. Again, the total volume was 20 µL.

Samples were incubated at 37° C. for 1 hour. Then, the transferase reaction was terminated by heating at 70° C. for 10 min. Loading buffer 10 µL (98% formamide, 10 mM EDTA 1 mg/mL xylene cyanol and 1 mg/mL bromophenol blue) was added to each reaction mixture, and an aliquot containing 2 pmoles of products (4 µL) was resolved on 8% PAGE. An additional study was done testing just G-ONH$_2$ at 250 µM at 2, 5, 15, 30 and 60 min incubation at 37° C.

Figure 1:
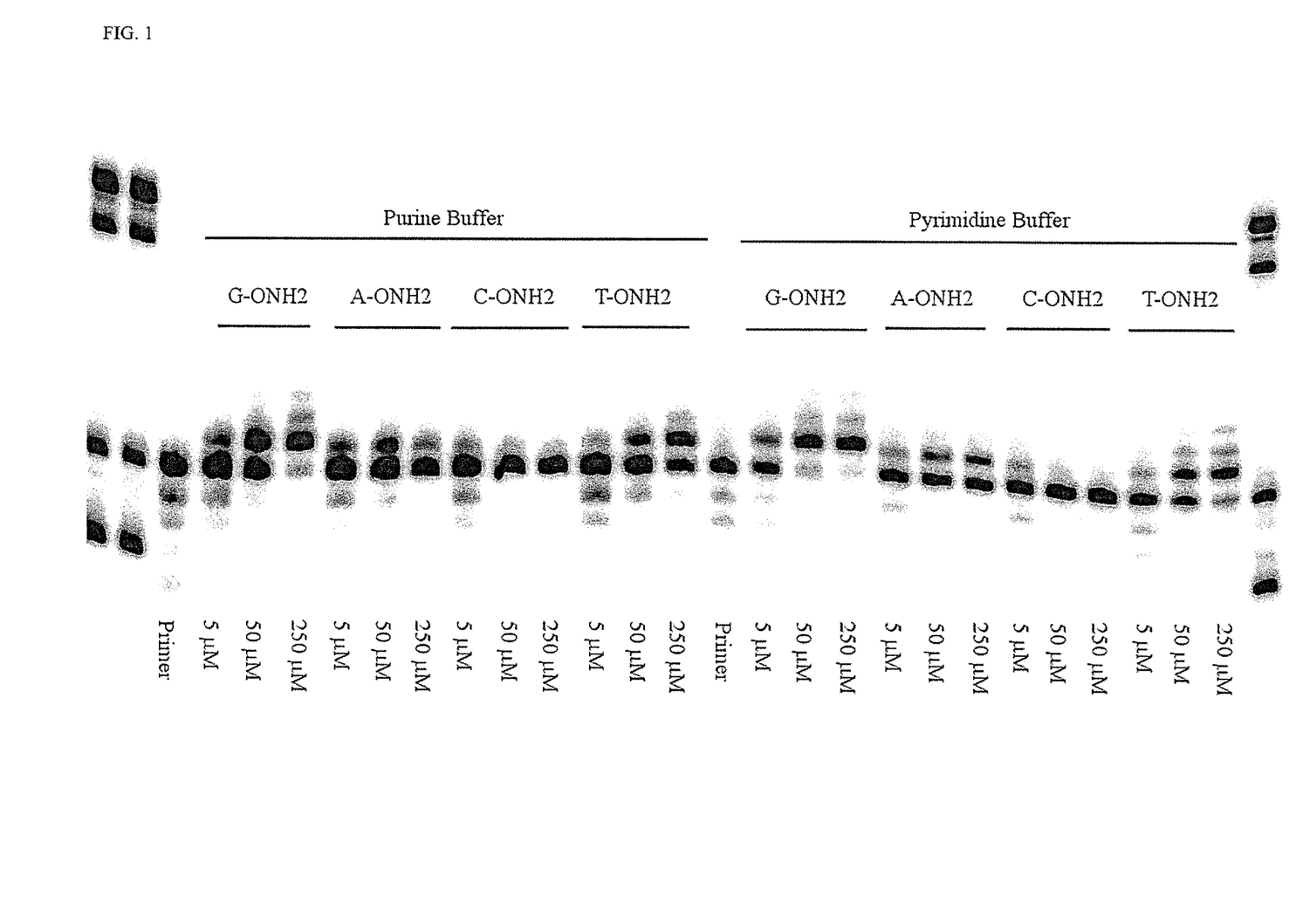
FIG. 1. A polyacrylamide gel electrophoresis (PAGE) image showing the addition by terminal deoxynucleotide transferase (TdT) of a single nucleotide carrying a 3'-$ONH_2$ group in two different buffers to an oligonucleotide carrying a 5'-phosphorus-32 label. External bands are ladders. The concentrations of the aminoxytriphosphates are shown below each lane, for the aminoxytriphosphate indicated at the top of each lane.

Data are shown in FIG. 1. Terminal transferase was able to incorporate all four nucleoside triphosphates containing the 3'-ONH$_2$ block. In the purine buffer, dGTP-ONH$_2$ appears to be incorporated more easily than dATP-ONH$_2$. However even though this buffer is sold commercially to prefer standard purine nucleosides over pyrimidine nucleosides, dTTP-ONH$_2$ is still incorporated. However, in purine buffer, dCTP-ONH$_2$ is only slightly incorporated, and appears to inhibit the reaction at higher concentrations.

In the pyrimidine buffer, dGTP-ONH$_2$ and dATP-ONH$_2$ both are successfully incorporated, as is dTTP-ONH$_2$. dCTP-ONH$_2$ is perhaps incorporated better, but again appears to have inhibitory activity.

The results in FIG. 1 were obtained with triphosphates containing a small amount of 3'-OH unblocked nucleoside triphosphates. The bands indicating incorporation of more than one nucleotide indicate this.

Figure 2:
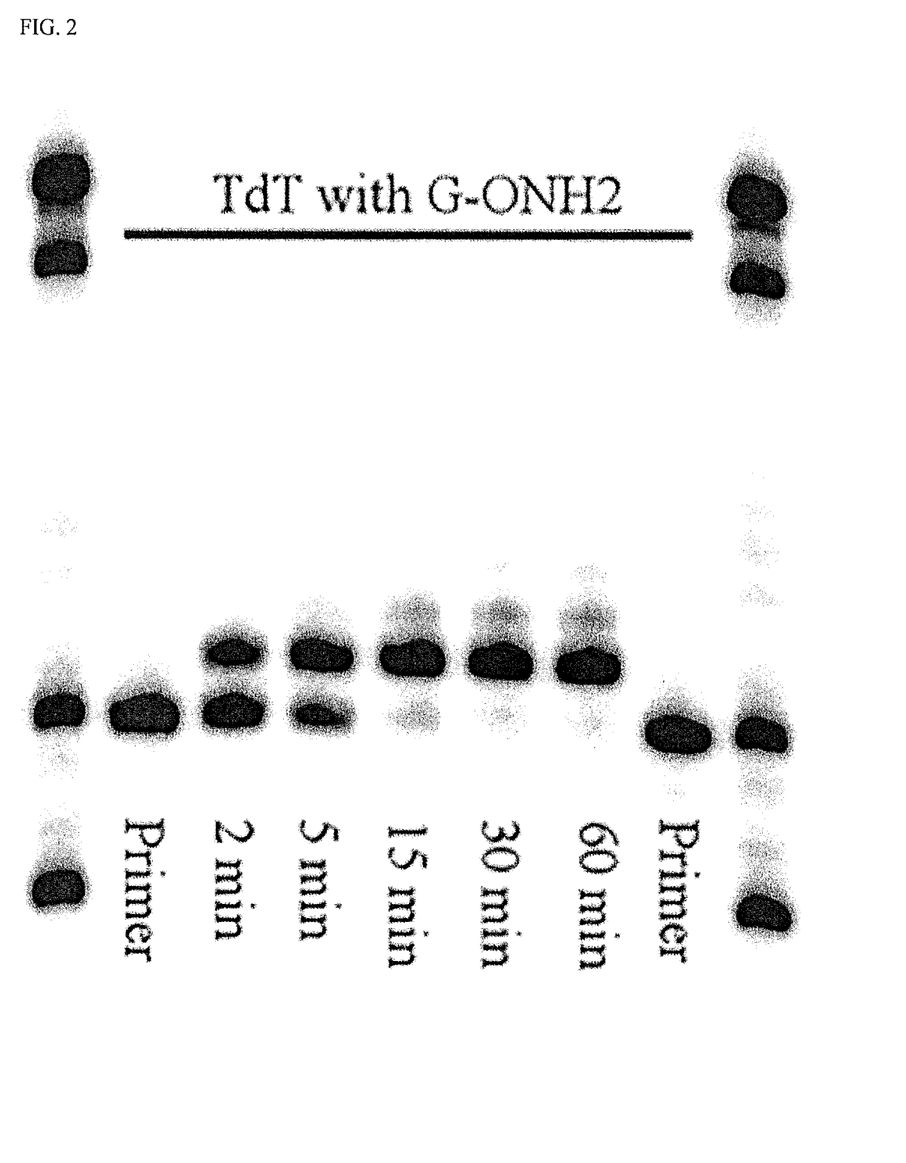
FIG. 2: PAGE (16%) showing a time course of GTP-$ONH_2$ incorporation using terminal transferase (TdT). Addition of a single nucleotide is complete at ca. 15 minutes. This preparation contains substantial amounts of dGTP having a free 3'-OH group, as indicated by the second shadow band.

A time course for the incorporation of GTP-ONH$_2$ using TdT was then determined (FIG. 2). Nearly all of the primer has acquired an additional oligonucleotide) is seen. Thus, contacting oligonucleotide with the triphosphates is shown to be a way to incorporate the reversible terminator without the need of a template.

Example 2

Figure 3:
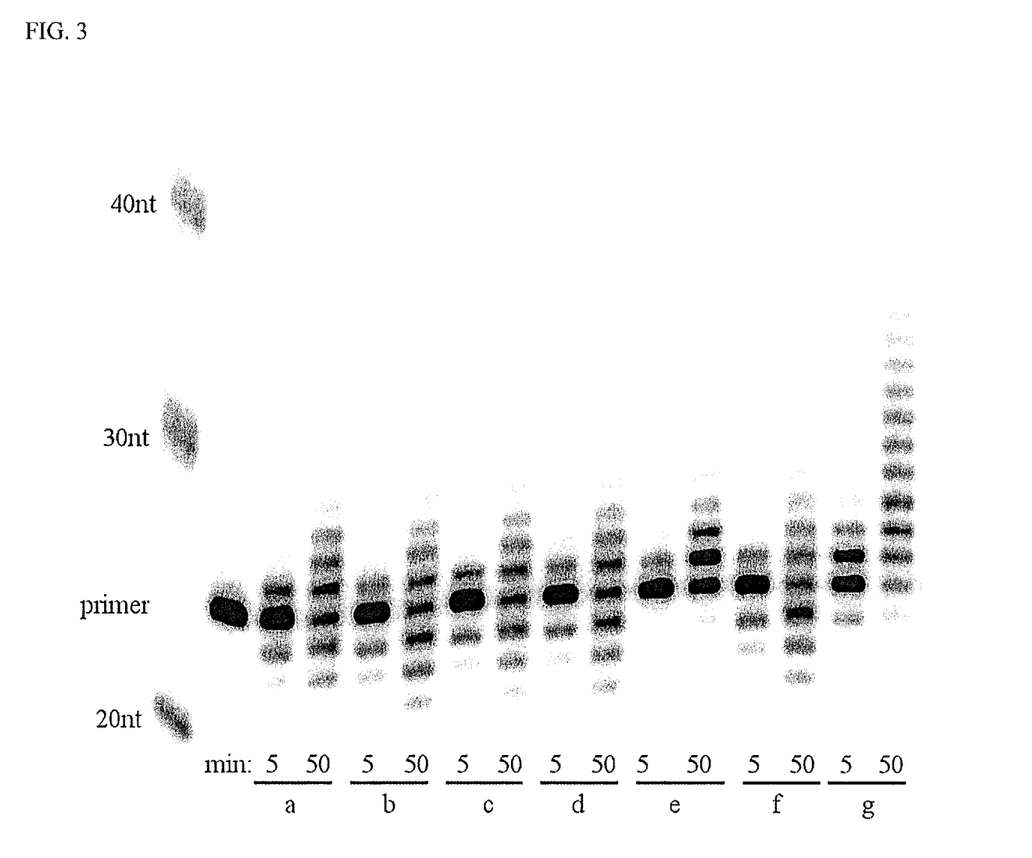
FIG. 3. PAGE (20%) of aminoxy samples tested in terminal transferase reaction to extend a 5'-radiolabeled primer. Lanes labeled a through g have different triphosphates as described in the text; incubation times are 5 and 50 minutes, as indicated.

The oligonucleotide primer used here is the same as in Example 1. The aminoxytriphosphates were prepared on a resin, as taught in U.S. patent application Ser. No. 15/460, 475, but under a release procedure using HONH$_2$ elution, which did not minimize the presence of contaminating triphosphates with a free 3'-OH group. This shows the results of this procedure. Data are shown in FIG. 3. The lanes are as follows:

(a) The aminoxytriphosphate was synthesized on resin, with no Tris washes, and with immediate elution of the triphosphate with HONH$_2$ after synthesis (b) The aminoxytriphosphate was synthesized on resin, with no Tris washes. The resin was then stored at room temperature overnight. Then, the triphosphate was eluted using HONH$_2$ and used.

(c) The aminoxytriphosphate was synthesized on resin, with three Tris washes overnight for one hour each. The aminoxytriphosphate was then eluted with HONH$_2$.

(d) The aminoxytriphosphate was synthesized on resin, which was then stored at room temperature overnight. The resin was then washed with Tris buffer (thrice, each for 1 hour). The aminoxytriphosphate was then eluted with HONH$_2$.

(e) The TdT extension was done with standard aminoxytriphosphate prepared in solution, a preparation that HPLC analysis showed contains ~0.5% 3'-OH.

(f) The TdT extension was done with standard aminoxytriphosphate prepared in solution, following in situ deprotection of the acetoxime with HONH$_2$, with buffer concentrations as in (a-d)

(g) The same as in (f), but spiked with 2% TTP-OH containing a free 3'-hydroxyl group.

The TdT reaction was carried out as before with $^{32}$P-labeled primer (0.5 µM) in 1× in terminal transferase buffer (20 mM Tris-acetate, pH 7.9, 50 mM potassium acetate, 10 mM magnesium acetate, 1 mM dithiotheritol), 0.25 mM CoCl$_2$, 200 µM reversible terminator samples (a-f) and 10 Units of terminal deoxynucleotidyl transferase (TdT). Reactions were incubated at 37° C. for five and 50 min. Reactions were quenched by the addition of formamide quench buffer and were resolved on a 20% PAGE (FIG. 3).

Example 3

Figure 4:
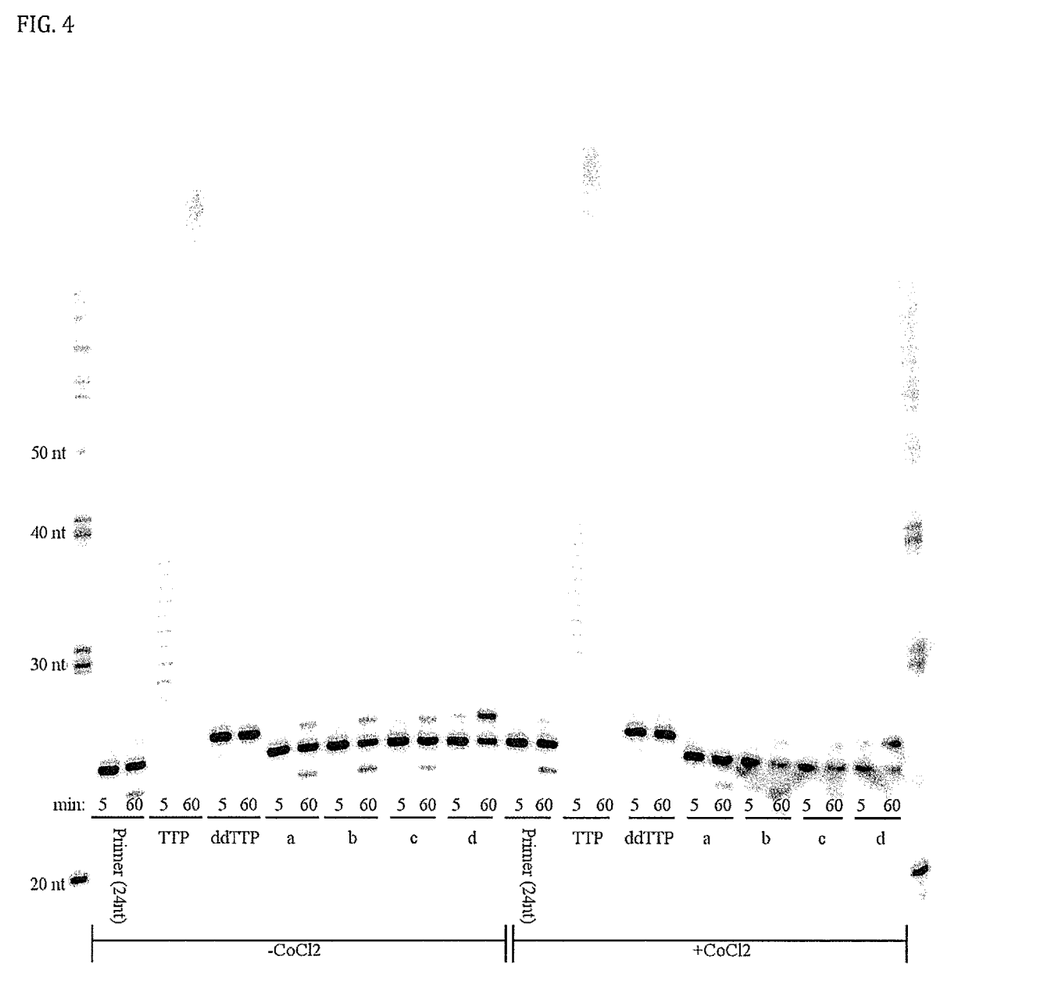
FIG. 4. PAGE (20%) of control and aminoxy triphosphates prepared as taught in U.S. patent application Ser. No. 15/460,475 tested in a terminal transferase reaction in two different buffers. This data set shows no significant impact of the presence of divalent cobalt cation in the incubation buffer.

The TdT reaction was executed with dTTP-ONH$_2$ prepared as taught in U.S. patent application Ser. No. 15/460, 475 using the same primer as above. Here, the aminoxytriphosphates were prepared by releasing TTP-ONH$_2$ from the resin using MeONH$_2$. Data are shown in FIG. 4.

(a) TTP-ONH$_2$, crude from resin synthesis, with MeONH$_2$ buffer (4.2 mM).
(b) TTP-ONH$_2$, pure from solution synthesis, with MeONH$_2$ buffer (5 mM).
(c) TTP-ONH$_2$, pure from solution synthesis, HPLC purified, no MeONH$_2$ buffer, in pure water (4 mM).
(d) dGTP-ONH$_2$, pure from solution synthesis, HPLC purified, no MeONH$_2$ buffer, in pure water (5 mM)

As before, $^{32}$P labeled primer (0.5 µM) in 1× in terminal transferase buffer (20 mM Tris-acetate, pH 7.9, 50 mM potassium acetate, 10 mM magnesium acetate, 1 mM dithiotheritol), with and without 0.25 mM CoCl$_2$, 200 µM reversible terminator samples (a-d) and 10 Units of terminal deoxynucleotidyl transferase (TdT). Control samples containing TTP and ddTTP were also tested. Reactions were incubated at 37° C. 5 and 60 min. Reactions were quenched by the addition of formamide quench buffer and were resolved on a 20% PAGE (FIG. 4).

Example 4

| 1) Terminal transferase 3'- tailing studies | |
|---|---|
| Primer dhSSP1 | SEQ ID NO 1 |
| 5'-GCG TAA TAC GAC TCA CTA TGG ACG-3' | |
| Aminoxy samples | |
| terminator | purity (at 260 nm) |
| dATP-ONH$_2$ | 67% |
| dCTP-ONH$_2$ | 74% |
| TTP-ONH$_2$ | 78% |
| TTP-ONH$_2$ in dH$_2$O | |
| dGTP-ONH$_2$ | 76% |
| dSTP-ONH$_2$ | |

Figure 7:
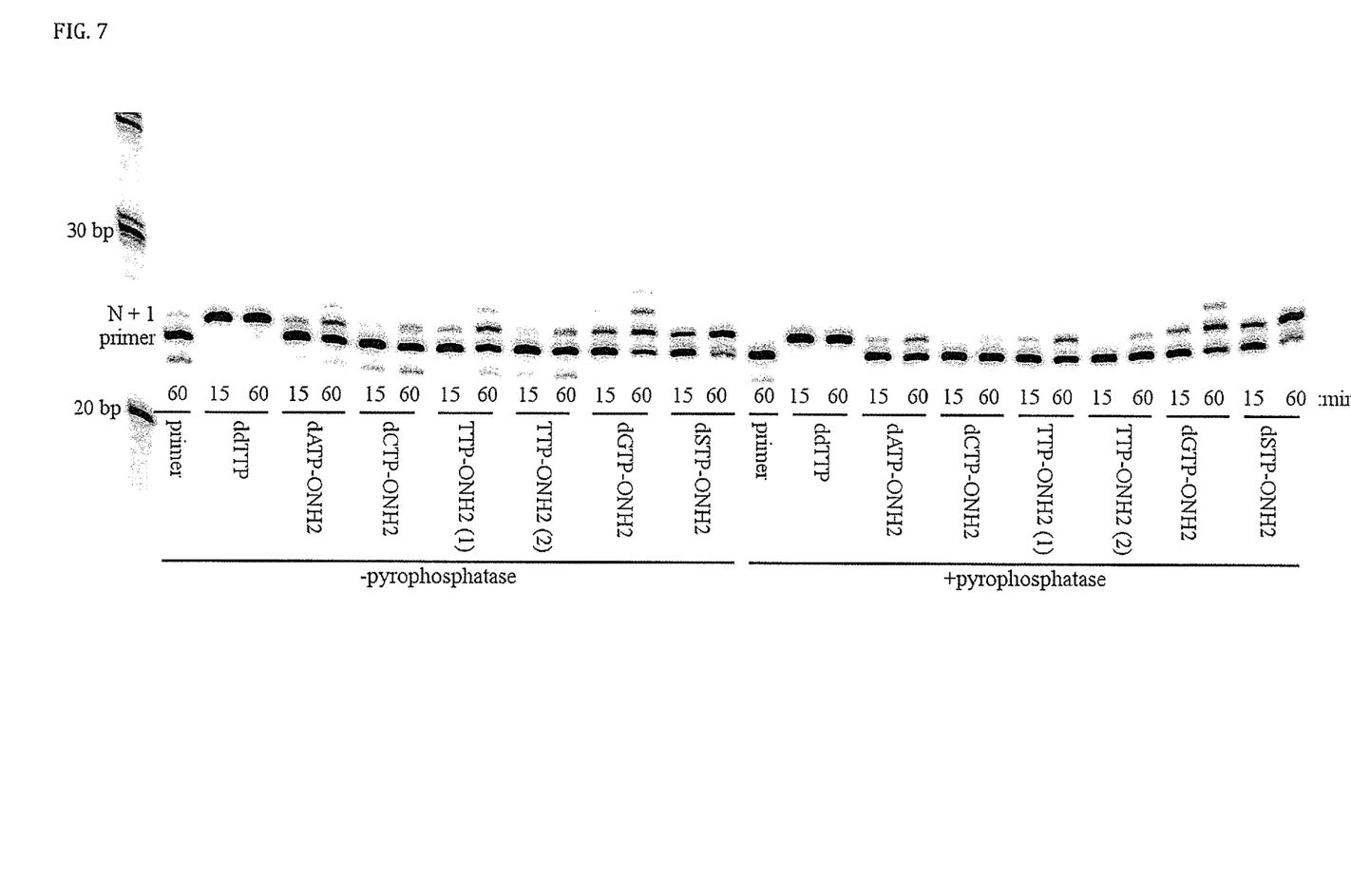
FIG. 7. PAGE (20%) of aminoxy reversibly terminated and irreversible triphosphate tested in terminal transferase reactions in the absence and presence of pyrophosphatase. Reactions were incubated for 15 and 60 min.
Figure 8:
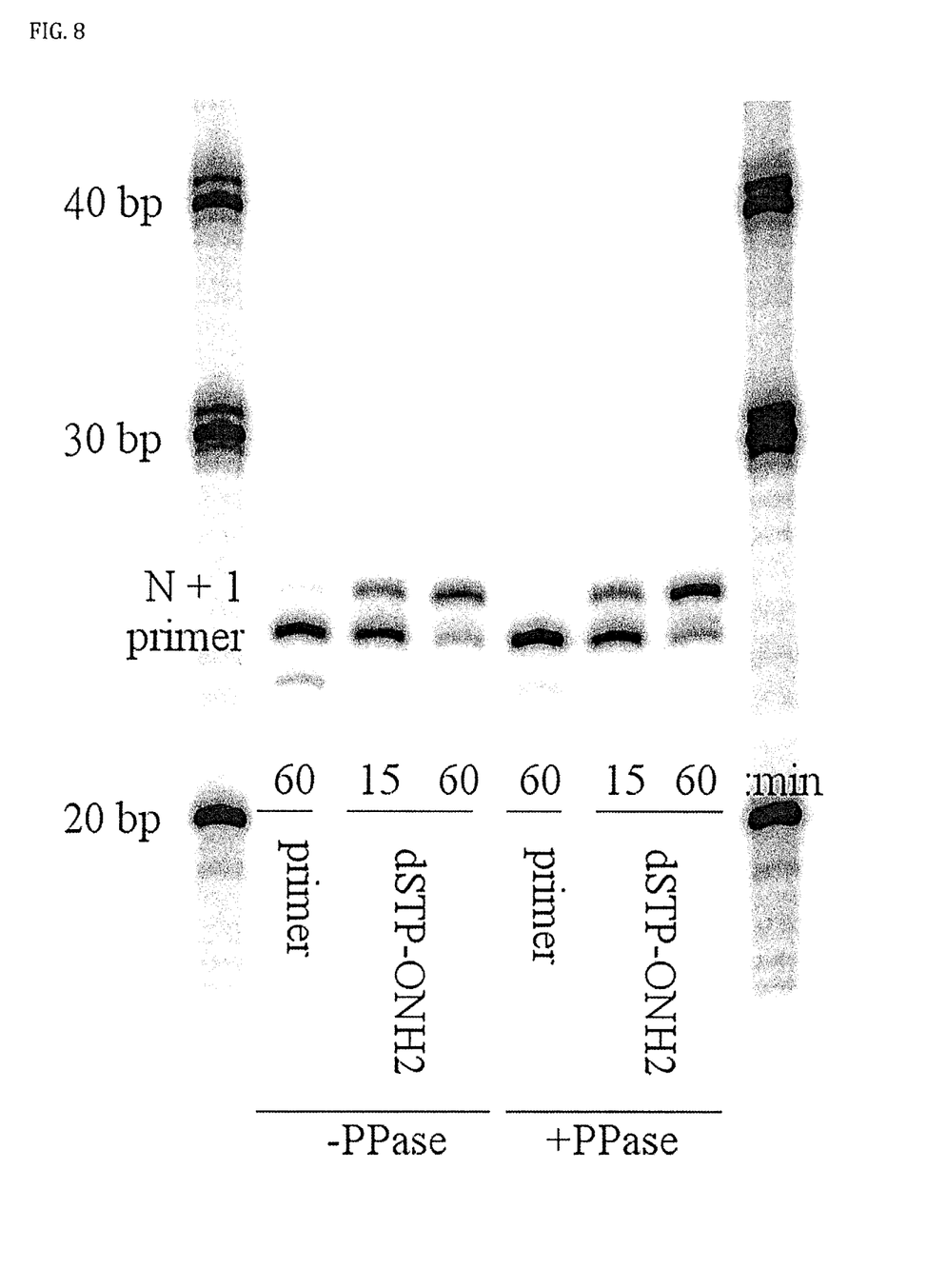
FIG. 8. PAGE (20%) of dSTP-$ONH_2$ without and with pyrophosphatase tested in terminal transferase reactions. Reactions were incubated for 15 and 60 min.

Radiolabeled γ$^{32}$P dhSSP1 (0.5 µM) in 1× in terminal transferase buffer (20 mM Tris-acetate, pH 7.9, 50 mM potassium acetate, 10 mM magnesium acetate, 1 mM dithiotheritol), 0.25 mM CoCl$_2$, 200 µM reversible terminator samples or irreversible terminator and 0.5 U/µL of terminal deoxynucleotidyl transferase (TdT) without and with the addition of pyrophosphatase (0.05 Units in 20 µL reaction). Reactions were incubated at 37° C. 15 and 60 min. As a control, primer samples contained terminal transferase but lacked the addition of triphosphate. Reactions were quenched by the addition of formamide quench buffer and were resolved on a 20% PAGE (FIG. 7). Another gel was run to resolve the dSTP-ONH$_2$ queried samples (FIG. 8).

Figure 9:
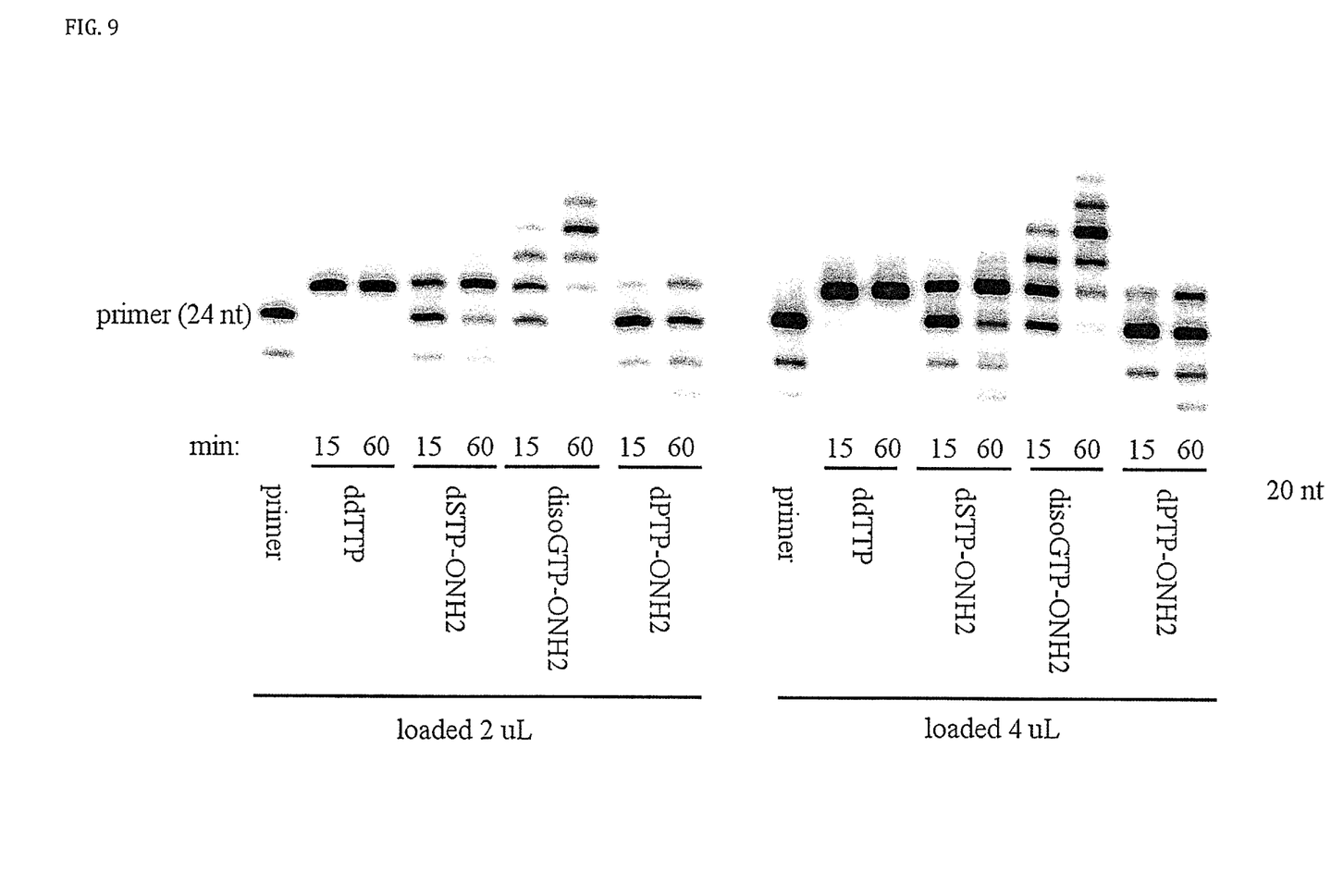
FIG. 9. PAGE (20%) of extension of primers using terminal transferase and AEGIS nucleotides "S" (a pyrimidine analog presenting an acceptor-acceptor-donor hydrogen bonding pattern), "B" (a purine analog presenting a donor-donor-acceptor hydrogen bonding pattern) and "P" (a purine analog presenting a donor-donor-acceptor hydrogen bonding pattern). aminoxy samples (tested in terminal transferase reactions. Reactions were incubated for 15 and 60 min. The tailing oligo is 24 bases long. Left panel was loaded 2 µL of samples; right panel was loaded 4 µL of samples.

Separately, a reaction was run with radiolabeled γ$^{32}$P dhSSP1 (0.1 µM) in 1× in terminal transferase buffer (20 mM Tris-acetate, pH 7.9, 50 mM potassium acetate, 10 mM magnesium acetate, 1 mM dithiothreitol), 0.25 mM CoCl$_2$, 200 µM reversible terminator samples or irreversible terminator and 1 U/µL of terminal deoxynucleotidyl transferase TdT). Reactions were incubated at 37° C. 15 and 60 min. As a control, primer samples contained terminal transferase but lacked the addition of triphosphate. Reactions were quenched by the addition of formamide quench buffer and were resolved on a 20% PAGE (FIG. 9).

What is claimed is:

1. A process for synthesizing an oligonucleotide that has a 3'-ONH$_2$ moiety instead of a 3'-OH moiety, said process comprising contacting an oligodeoxyribonucleotide in an aqueous buffered solution with terminal deoxynucleotide transferase and a nucleoside triphosphate having the structure:

or one of its ionized forms, wherein B is a heterocycle selected from the group consisting of

-continued wherein Su indicates the point of attachment of the heterocycle to the sugar, and wherein said solution contains less than 1 micromolar hydroxylamine.

2. A process for synthesizing an oligonucleotide that has a 3'-ONH$_2$ moiety instead of a 3'-OH moiety, said process comprising contacting an oligodeoxyribonucleotide in an aqueous buffered solution with terminal deoxynucleotide transferase and a nucleoside triphosphate having the structure:

or one of its ionized forms, wherein B is a heterocycle selected from the group consisting of wherein Su indicates the point of attachment of the heterocycle to the sugar, and R is either H, CH$_3$, or a functionalized side chain; wherein said solution contains less than 1 micromolar hydroxylamine.

3. The process of claim 2, wherein said heterocycle is wherein Su indicates the point of attachment of the heterocycle to the sugar, and R is either H, CH$_3$, or a functionalized side chain.

4. The process of claim 2, wherein said heterocycle is wherein Su indicates the point of attachment of the heterocycle to the sugar, and R is either CH3, or a functionalized side chain.

5. The process of claim 2, wherein B is wherein Su indicates the point of attachment of the heterocycle to the sugar.

6. A process for synthesizing an oligonucleotide that has a 3'-ONH$_2$ moiety instead of a 3'-OH moiety, said process comprising contacting an oligodeoxyribonucleotide in an aqueous buffered solution with terminal deoxynucleotide transferase and a nucleoside triphosphate having the structure:

or one of its ionized forms, wherein B is a heterocycle selected from the group consisting of wherein Su indicates the point of attachment of the heterocycle to the sugar," wherein said solution contains less than 1 micromolar hydroxylamine.

* * * * *